(12) United States Patent
Chong et al.

(10) Patent No.: US 11,419,727 B2
(45) Date of Patent: Aug. 23, 2022

(54) SEMI-AUTOMATED IMAGING RECONSTRUCTION FOR ORBITAL FRACTURE REPAIR

(71) Applicant: The Chinese University of Hong Kong, Hong Kong (CN)

(72) Inventors: Kelvin Kam-lung Chong, Hong Kong (CN); Chun Sing Chui, Hong Kong (CN); Wing Hing Ringo Cheung, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 380 days.

(21) Appl. No.: 16/782,558

(22) Filed: Feb. 5, 2020

(65) Prior Publication Data
US 2020/0261231 A1 Aug. 20, 2020

Related U.S. Application Data

(60) Provisional application No. 62/807,480, filed on Feb. 19, 2019.

(51) Int. Cl.
*A61F 2/30* (2006.01)
*G06T 17/00* (2006.01)
(Continued)

(52) U.S. Cl.
CPC ...... *A61F 2/30942* (2013.01); *A61B 17/0231* (2013.01); *A61F 2/2875* (2013.01);
(Continued)

(58) Field of Classification Search
CPC .... A61F 2/30942; A61F 2/2875; G06T 7/149; G06T 5/008; G06T 7/0012; G06T 17/00;
(Continued)

(56) References Cited

U.S. PATENT DOCUMENTS 8,281,638 B2 * 10/2012 Metzger ............... A61F 2/2875
72/413
8,644,578 B1 * 2/2014 Wiley ................ G06K 9/6255
382/131

(Continued)

OTHER PUBLICATIONS

Kang, Sunah, et al. "Generation of customized orbital implant templates using 3-dimensional printing for orbital wall reconstruction." Eye 32.12 (2018): 1864-1870. (Year: 2018).*

(Continued)

*Primary Examiner* — Utpal D Shah
(74) *Attorney, Agent, or Firm* — Kilpatrick Townsend & Stockton LLP

(57) ABSTRACT

Techniques for fabrication of implant material for the reconstruction of fractured eye orbit may include using an image processing system to analyze a set of two-dimensional images representing a three-dimensional scan of a skull of a patient, automatically detect an orbital fracture in the skull based on the set of two-dimensional images, and identify which/both of the two eye orbits containing any orbital fracture. The techniques may further include, for each of the two-dimensional images in which the orbital fracture is detected, determining a region of interest, and extracting the region of interest. The techniques may further include generating a three-dimensional reconstruction model for the fractured eye orbit, and outputting model data for generating an implant mold for the fractured eye orbit.

20 Claims, 11 Drawing Sheets

(51) Int. Cl.
  G06K 9/62    (2022.01)
  G06T 5/00    (2006.01)
  G06T 7/149   (2017.01)
  A61B 17/02   (2006.01)
  A61F 2/28    (2006.01)
  G06T 7/00    (2017.01)
  A61B 17/00   (2006.01)

(52) U.S. Cl.
  CPC ......... *G06K 9/6228* (2013.01); *G06K 9/6256* (2013.01); *G06T 5/008* (2013.01); *G06T 7/0012* (2013.01); *G06T 7/149* (2017.01); *G06T 17/00* (2013.01); *A61B 2017/0042* (2013.01); *A61B 2017/00526* (2013.01); *A61F 2002/2878* (2013.01); *A61F 2002/30948* (2013.01); *A61F 2002/30952* (2013.01); *A61F 2002/30957* (2013.01); *A61F 2002/30985* (2013.01); *G06T 2207/20081* (2013.01); *G06T 2207/20116* (2013.01); *G06T 2207/30008* (2013.01); *G06T 2207/30041* (2013.01); *G06T 2210/41* (2013.01); *G06V 2201/033* (2022.01)

(58) Field of Classification Search
  CPC . A61B 17/0231; G06K 9/6228; G06K 9/6256
  See application file for complete search history.

(56) References Cited

U.S. PATENT DOCUMENTS

| | | | | |
|---|---|---|---|---|
| 11,263,749 | B1* | 3/2022 | Purushottam | G16H 30/40 |
| 2022/0085401 | A1* | 3/2022 | Lu | B01J 20/20 |

OTHER PUBLICATIONS

Becker, Matthias, et al. "Development of a reliable method for orbit segmentation & measuring." 2015 IEEE International Symposium on Medical Measurements and Applications (MeMeA) Proceedings. IEEE, 2015. (Year: 2015).*

"Next Generation Approach to Orbital Lesion Removal and Reconstruction" at The 4th JEC International Meeting 2020 (Jakarta, Indonesia), Feb. 6-8, 2020.

"Next-Generation Orbital Tumor Removal and Reconstruction" (Senior Author) at American Academy of Ophthalmology (AAO) 2019 (San Francisco, USA), Oct. 12-15, 2019.

"It's Next Generation Orbital Surgeries" at 3rd Tri-Society Head and Neck Oncology Meeting 2019 (Hong Kong), Aug. 30, 2019-Sep. 1, 2019.

"Next generation orbital surgeries" at the Fifth International Conference of Ophthalmic Endoscopic Surgery (5th ICOES) (Changchun city, China), Jun. 27-30, 2019.

"Next Generation Orbital Tumour Removal" in session European Society of Ophthalmic Plastic and Reconstructive Surgery (ESOPRS) at European Society of Ophthalmology (SOE 2019) (Nice, France), Jun. 13-16, 2019.

"Transantral Endoscopy and 3D-Printing as Operative Adjuncts in Large Orbital Blow-Out Fractures" at Asia-Pacific Academy of Ophthalmology Congress (Bangkok, Thailand), Mar. 6-9, 2019.

"Next generation orbital apical tumor removal and reconstruction" at 4th International Conference of Ophthalmic Endoscopic Surgery (ICOES) (Wenzhou, China), Nov. 22-25, 2018.

"3D-Printing for Surgical Instrument and Orbital Moulds (3SIOM) for Orbital Fracture Repair" at ASOPRS 49th Annual Fall Scientific Symposium (Chicago, USA), Oct. 25-26, 2018.

"3D printing assisted orbital fracture repair and reconstruction", Cape Town and Pretoria Annual Symposiums (South Africa), Oct. 18-21, 2018.

"Next Generation Orbital tumor removal and reconstruction" at Asia-International Society of Ocular Oncology Conference 2018 (Shanghai), Oct. 12-14, 2018.

"3D Printing in Orbital Fracture Repair", Engineering Medical Innovation Summit: Medicine for the Future 2018, Aug. 18, 2018, Science Park.

"3D Printing in Orbital Fracture Repair" at The First Hong Kong International Interdisciplinary Clinical 3D Printing Forum 2018 (Med3DP), Science Park Hong Kong, Jul. 27, 2018.

* cited by examiner

Original DICOM image

Original histogram

With contrast enhanced

Histogram after contrast enhancement

SEMI-AUTOMATED IMAGING RECONSTRUCTION FOR ORBITAL FRACTURE REPAIR

CROSS-REFERENCES TO RELATED APPLICATIONS

This application claims the benefit of priority to U.S. Provisional Application No. 62/807,480, filed Feb. 19, 2019, the entire contents of which is incorporated herein by reference.

BACKGROUND

Existing techniques for surgical reconstruction of the fractured orbit poses challenges that are different from the rest of the body. As orbital bones are among the thinnest in the human body, signal contrast of the orbital bones from the adjacent tissues (e.g. paranasal sinuses) can be poor in medical images. Thus, there is an inherent difficulty in identifying and delineating the complete extent of orbital fracture in these images. Therefore, reconstruction of three-dimensional (3D) model of the orbital region for reconstructive purposes has exclusively been done manually. This process of segmentation is time-consuming and requires intensive input from both clinicians and engineers. The most widely used medical imaging modality in orbital fracture is computerized tomography (CT) scan which relies on X-ray technology. Among the various bony structures of the orbital region, the medial and inferior walls are the thinnest and in turn most commonly fractured. The CT images over these two regions are therefore of the lowest contrast. Detection of bone fractures over these commonly fractured regions is particularly difficult. On the other hand, current process of manual segmentation and reconstruction of any 3D model from multiple two-dimensional (2D) scan images is also extremely labor-intensive. This remains the rate-limiting step in generating a 3D model for operative planning in orbital fracture repair.

BRIEF SUMMARY

Before fabrication of an anatomical model to assist the reconstruction of fractured orbit, an image processing system is used to analyze a set of two-dimensional medical images (typically CT scans) of the orbits of a patient. The system is designed to automatically detect the presence of orbital fracture based on the two-dimensional images, and to identify which or both orbits as suffering from any fracture. The system may, for each of the two-dimensional images in which orbital fracture is detected, determine the region of interest (ROI) where the orbital fracture is located, and extract the ROI. The system may then generate a three-dimensional reconstruction model for the fractured orbit, and output the model data (e.g., stereolithographical file format) for generating an implant mold for the fractured eye orbit. The system may further provide data for 3D printing the implant mold which can be used to fabricate an orbital implant to cover the orbital bone defect. An orbital tissue retractor can also be fabricated using the 3D model data.

The image processing system can be trained to detect the orbital fracture using multiple orbital images with and without fractures. For example, the image processing system can be trained to detect any discontinuity of orbital bone structures and/or prolapse of orbital tissue into surrounding sinuses as indications of the orbital fracture. Generating the three-dimensional reconstruction model may include, for each of the two-dimensional images in which the orbital fracture is detected, adaptively enhancing contrast along the extracted region of interest (fractured areas), converting greyscale color into a binary black and white, and/or segmenting irregular boundaries using an active contour algorithm. Generating the three-dimensional reconstruction model may also include applying a marching cubes algorithm to generate an isosurface for the three-dimensional model.

An orbital implant fabricated using the above techniques may conform to the preinjured topography of the fractured orbit of the patient. An orbital retractor fabricated using the techniques may include a handle portion, and a tip portion that also conforms to the topography of an eye orbit of the patient.

An image processing system may include a processor, and a memory coupled to the processor. The memory may store a set of instructions, which when executed by the processor, causes the image processing system to perform some or all techniques for fabrication of implant material by the reconstruction of the fractured orbit. A non-transitory computer readable medium may store code, which when executed by a processor, implements the various operations of these techniques.

DETAILED DESCRIPTION

Various aspects of the present invention relate to the design of patient-specific orbital implants and instruments, and the process involved in production of such implants. In particular, techniques for 3D modelling anatomical models for reconstruction of orbital fracture using image-processing are described herein. The image-processing algorithms are automated as much as possible to shorten the time from clinical imaging to surgical implantation. These processes include automated detection of orbital fracture from medical images (e.g., CT images), identifying and cropping the region of interest (ROI) for further processing, segmentation of the orbital bony ROI using image processing techniques, reconstruction of the 3D model of the pre-fractured orbit from these segmented images, and output of the 3D model data for fabrication of the orbital models and instrument.

The 3D model is generated in stereolithographical file for 3D printing of the orbital molds and instruments.

Figure 1:
FIG. 1 illustrates an example of a computer tomography (CT) scan image showing a cross-section of a patient.

FIG. 1 illustrates an example of a computer tomography (CT) scan image showing a cross-section of the skull of a patient. The cross-section was taken along the axial/transverse direction from the chin moving upwards. The arrow in FIG. 1 is pointing to the right orbital region of the patient. As shown in FIG. 1, due to their extreme thinness, the medial and inferior walls of the bony orbit in CT images are always in very low contrast. This leads to extreme difficulty in identifying any orbital fracture or resolving the topography of the contralateral side intact orbit to build a reconstruction model specific for a particular patient.

Figure 2:
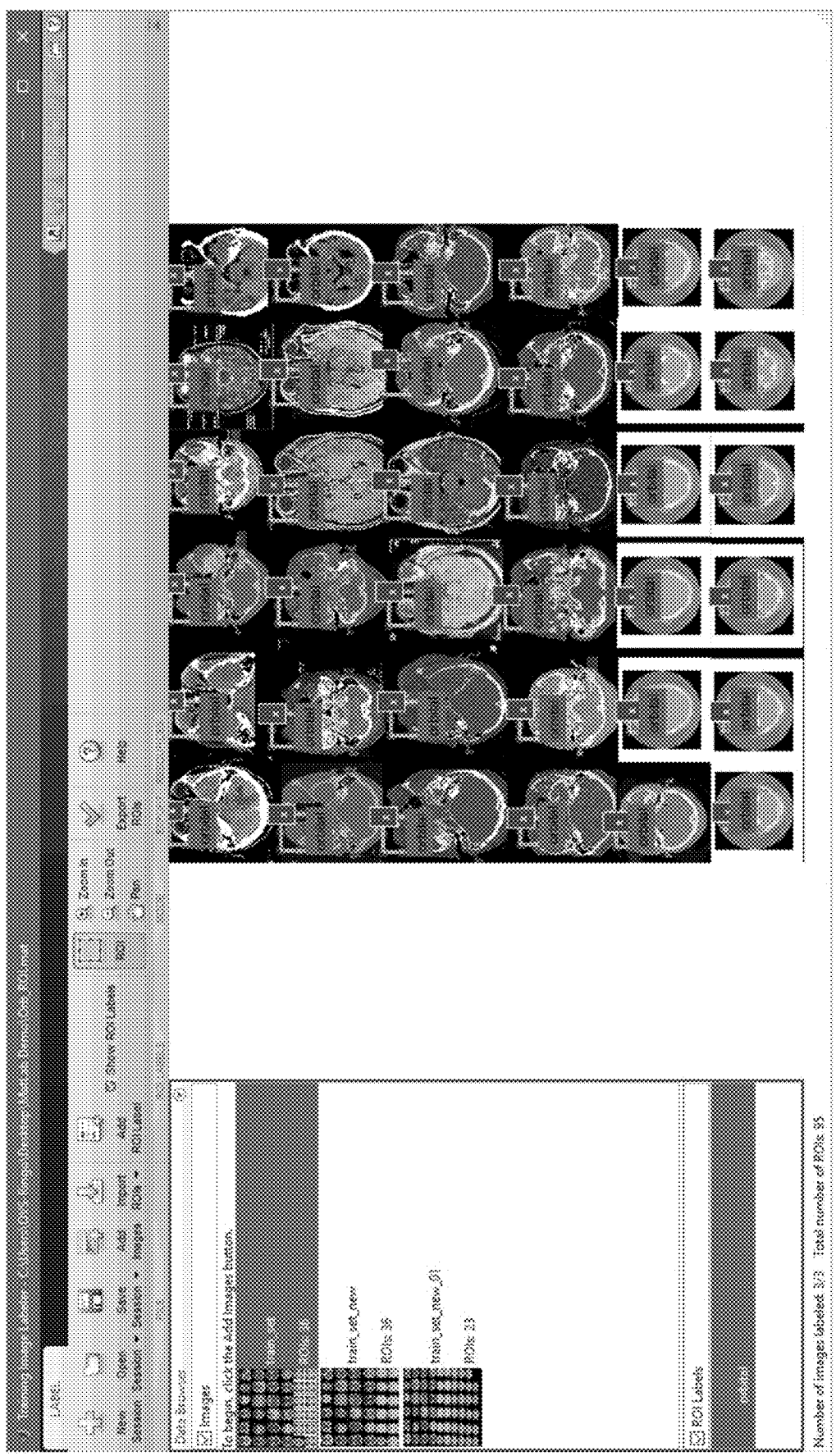
FIG. 2 illustrates a screen capture of a training session for orbital fracture detection.

To deal with the difficulty in detecting orbital bone fracture from CT images, machine learning can be employed to train an image processing system to distinguish between fractured and intact orbits. For example, around 100 or more orbital images can be inputted into the system as training data. These images can first be processed with their contrast enhanced for easier recognition. Both positive samples (those with fracture) and negative samples (those without fracture) are used. FIG. 2 illustrates a screen capture during a training session for orbital fracture detection. Properties in the CT images indicating the presence of orbital fracture include discontinued bony structure inside the orbital region, and/or prolapse of orbital soft tissue outside of the orbital region, both of which can be identified and characterized. For example, the number, location, size and/or depth of any bone discontinuities as well as orbital soft tissue outside the orbital region, correlation between these bony and soft tissues changes, structural deviation from the contralateral (opposite side) orbit, etc. can be characterized to generate a classifier that can be used to identify any orbital bone fracture.

Figure 3:
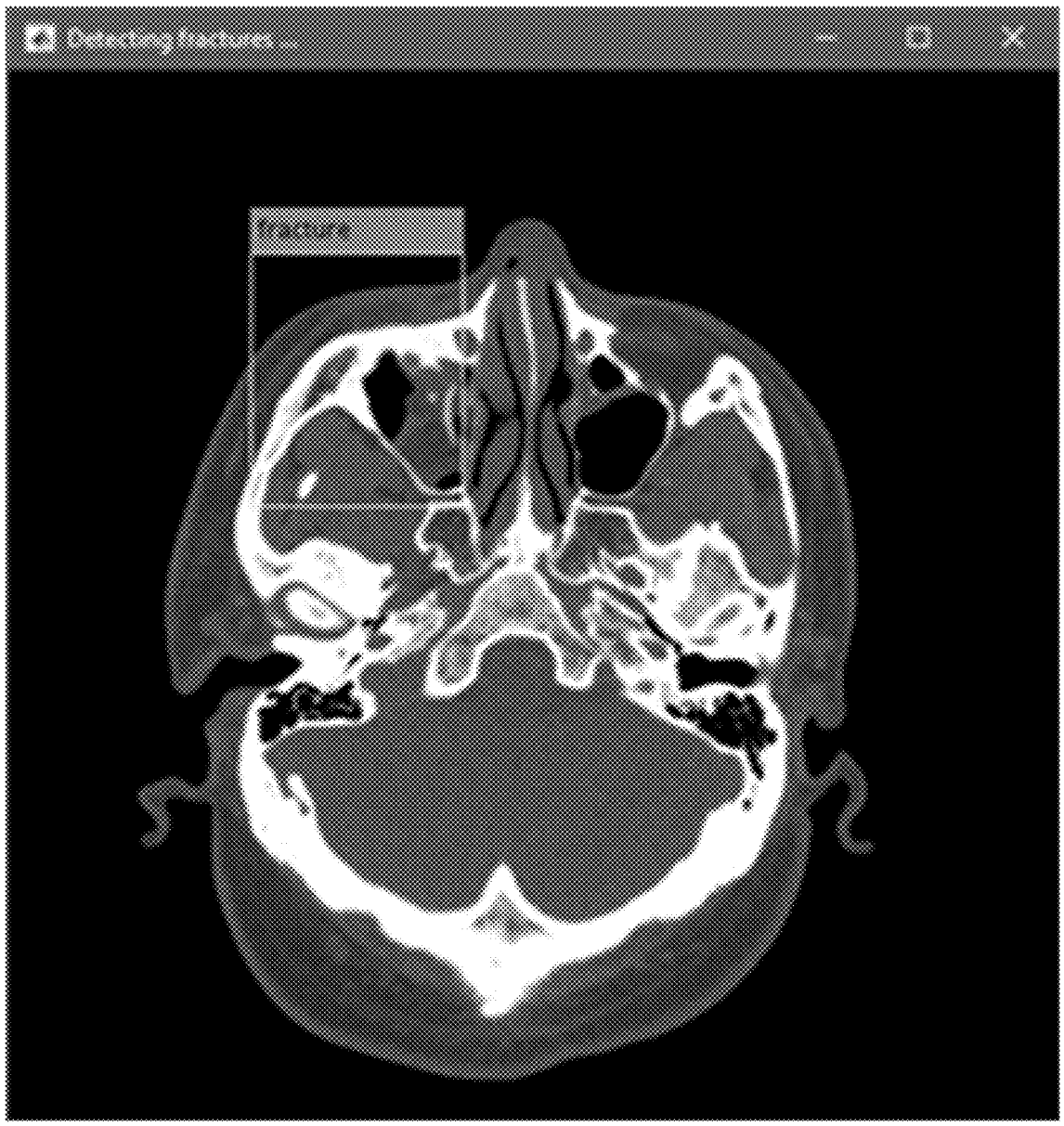
FIG. 3 illustrates an example of a CT scan image showing an orbital fracture.

FIG. 3 illustrates an example of a CT scan image showing an orbital fracture. Similar to FIG. 1, the cross section is taken along the axial/transverse direction from the chin moving upwards. As shown in FIG. 3, the highlighted region corresponding to the right eye orbit shows a significant amount of orbital soft tissue prolapsed outside of the orbital region into the surrounding paranasal sinuses. This is a clear indication of the presence of an orbital bone fracture. A comparison between the right eye orbit (fractured orbit) and the left eye orbit (intact orbit) also shows significant deviations from what should otherwise be a near-perfect mirror image in most healthy individuals. The presence of these changes in a set of orbital CT images can be used as indicators to detect the presence of orbital fracture in a patient.

Once the image processing system has been trained to detect orbital fractures using machine learning, medical (CT) images of the orbits of any new patient can be inputted into the system for analysis. Each medical image is a 2D cross-section (e.g., along the axial/transverse direction), and the set of 2D images represent the 3D shapes of the orbits of that patient. The set of 2D images need not scan the whole skull but will need to include the two orbits of each patient. The set of 2D orbital CT images can be read sequentially by the image processing system, and any of the images can be selected by a user (e.g., for a user to view an orbital bone fracture). If an orbital fracture is detected, additional processing steps can be performed to create a 3D mold using the image data to fabricate an anatomical model to assist in repairing the fracture. Additional processing can utilize a number of computer vision or image processing techniques, and can be implemented based on the MATLAB® application to leverage its image processing functions.

An image segmentation process can be used to crop out the region of interest (ROI) from the 2D images of the above CT orbit image set. Segmenting the images to crop out the ROI can reduce the image processing time by focusing on a smaller area. On the other hand, to further reduce processing time, irrelevant images (e.g., areas away from the fracture) can be omitted, and the ROI can be cropped from only the relevant images in the image set. The relevant images may include each of the 2D images in which orbital fracture is detected. In some circumstances, the relevant images may also include images that was scanned before the presence of orbital fracture (i.e. premorbid or pre-fracture scans). These additional images can be useful in verifying the reconstruction of a 3D anatomical model of the orbital structure surrounding the fracture.

The region of interest (ROI) in each image can be automatically determined by the image processing system. For example, the system may define the ROI by creating the smallest geometric shape (usually rectangle) around the fracture area. On the other hand, the ROI can be defined by a user manually highlighting the area of orbital fracture on the 2D images displayed on a user interface. The ROI in each image can then be mirrored to the intact (uninjured), contralateral orbit, and the corresponding ROI can then be cropped out from the intact orbit. This technique is referred to as "automatic mirror image overlay".

The cropped images including the fractured region(s) in the fractured orbit and the mirror images of the corresponding region from the intact (uninjured), contralateral orbit are extracted. They can be subjected to the following image enhancing processes. The contrast of the extracted images can be enhanced to increase the image quality and improve the distinction of the bony structures from the surrounding soft tissues or anatomical gaps (e.g. fissures or nerve canal) normally present inside the orbit. For example, a linear or non-linear transformation function can be applied globally to each extracted image to stretch the dynamic range of the grey level of each image, or a histogram equalization transformation can be applied globally to redistribute the grey level histogram of each extracted image to have a more uniform distribution. However, enhancing the contrast/signal of area(s) with weak contrasts/signals may overexpose areas with strong contrasts/signals. Alternatively, an adaptive contrast enhancement can be employed. For example, the reference range of the transformation function can be adjusted based on the intensities around each pixel so that the contrast enhancement is tailored locally for each pixel. In other words, a different transformation function can be applied to different portions in each extracted image to avoid over-contrasting. The histogram of each extracted image can be divided into dark, medium, and bright regions. Each region can be processed individually depending on the shape of the histogram of each region.

Figure 4:
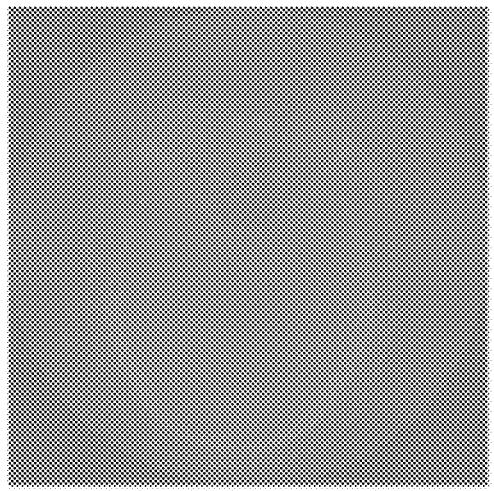
FIG. 4 illustrates an example of applying contrast enhancement to an orbital image.
Figure 4:
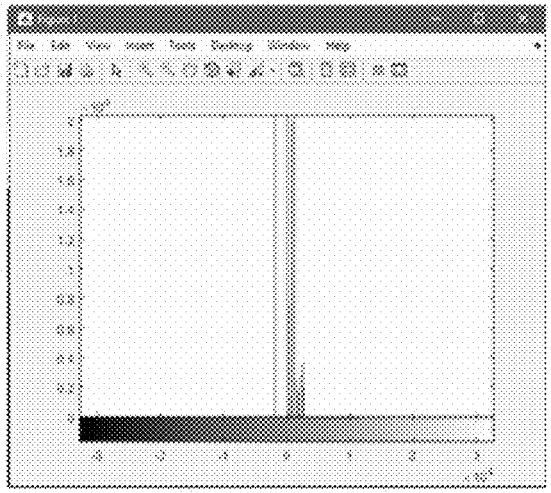
Figure 4:
Figure 4:
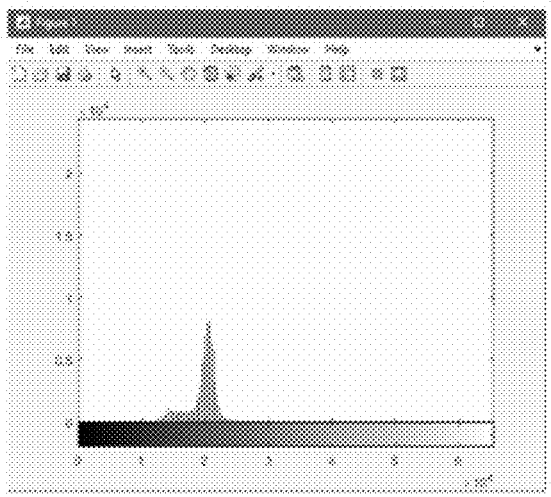

FIG. 4 illustrates an example of applying contrast enhancement to an orbital image. As shown in FIG. 4, the original image may have a large concentration of a few grey tones. Such an image may have a histogram with large peaks concentrated in a narrow band, and it can be difficult to distinguish orbital features in such an image. Applying contrast enhancement to the original image can reduce the peaks of the grey levels, shift the histogram distribution, and spread the tone of the image over a larger dynamic range. The resulting enhanced image can provide better clarity to the details of the physical structure of the orbital region.

After the contrast enhancement, a thresholding process can be performed to convert the extracted images from greyscale to binary black and white. The thresholding process can be used to partition an image into foreground (e.g., in white) and background (e.g., in black). For example, an intensity threshold value can be determined, and greyscale pixels with an intensity level equal to or greater than the threshold value can be converted to a white color and those below can be converted to a black color. The intensity threshold value can be set to the midpoint of the intensity range, to a median of the intensity histogram distribution, or to a value derived from empirical or prior results. To improve the thresholding process, the background of each extracted image can be darkened by using a top-hat filter to remove uneven background illumination prior to the thresholding process. This can improve the distinction between foreground and background and reducing the processing time for the thresholding process.

Figure 5:
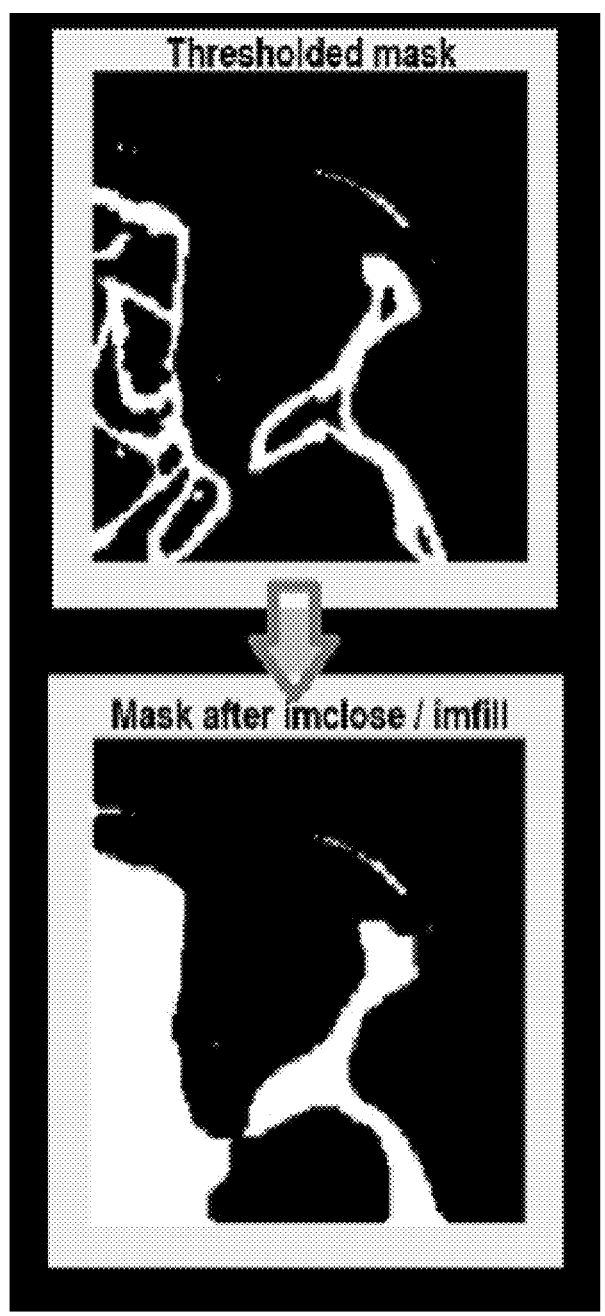
FIG. 5 illustrates an example of applying a hole-filling process to an orbit image.

After converting the extracted images to binary black and white according to an intensity threshold value, holes and irregularities may appear at the boundaries between the white foreground representing bone material and the black background. The upper image in FIG. 5 is an example of an image with holes and irregularities resulting from the thresholding process. To compensate for this, a hole-filling process can be performed to enclose the foreground regions. An active contour algorithm can be used to smooth the contour at the boundaries. The active contour algorithm may utilize an energy minimizing function to fit a curve with certain smoothness constraints onto an image resembling a boundary between the foreground and background. This can be taken as using a rubber band to wrap the target boundary to form the final contour to achieve the desirable segmentation. The extent or "tightness" of the wrapping depends on the number of iterations and the starting position of an initial seed. To achieve the best result, a pre-thresholded image boundary can be used as an initial seed contour so that the algorithm converges quickly (e.g., after a finite number of iterations such as 100) to the target boundary of the segmented images. An upper limit on the number of iterations can be set to reduce the processing time. The bottom image of FIG. 5 shows the results of applying the hole-filling process to the pre-thresholded upper image.

Figure 6:
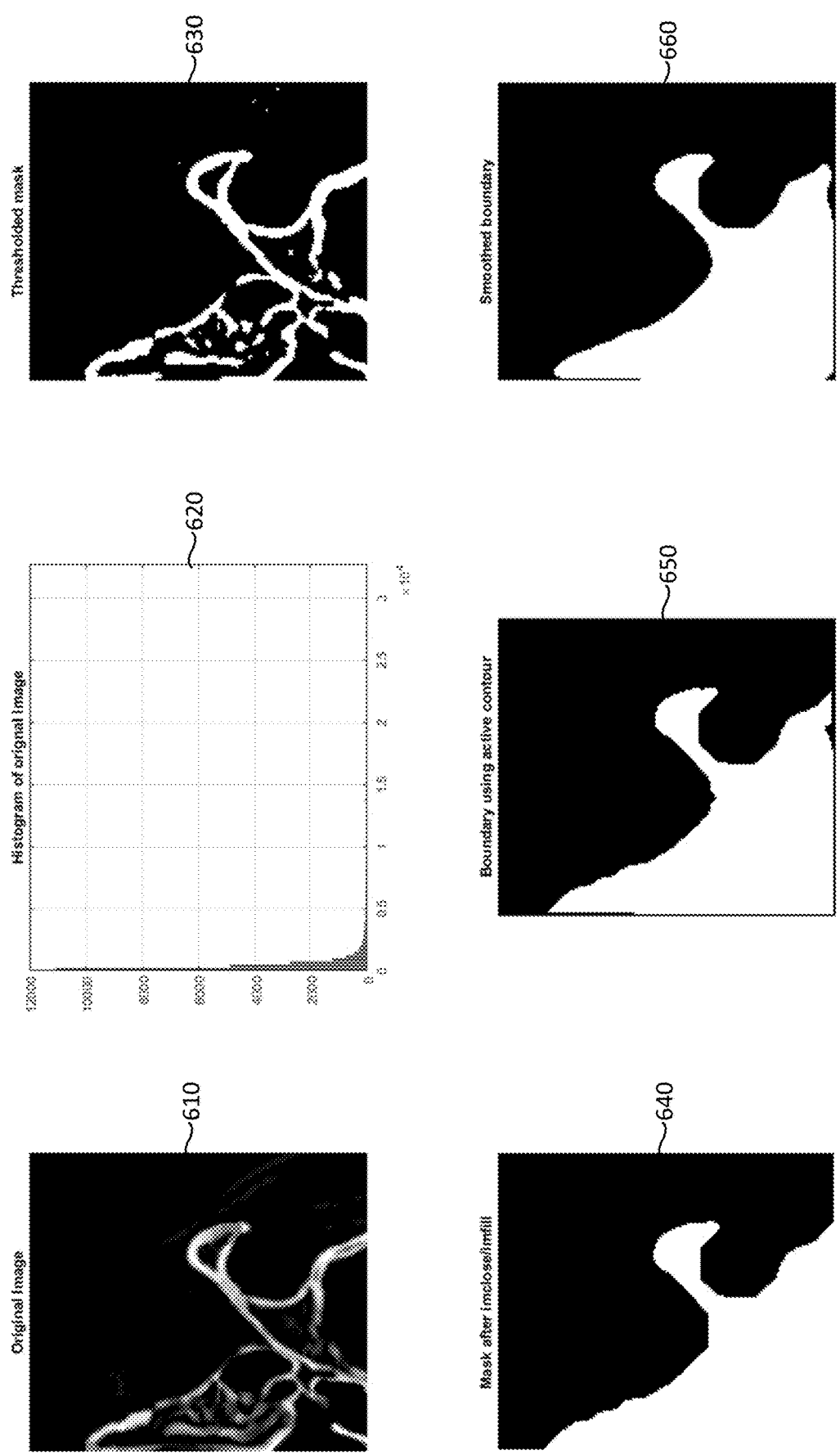
FIG. 6 illustrates an example of the different image processing techniques performed on a region of interest for segmentation.

FIG. 6 illustrates an example of the various image processing techniques performed on a region of interest (ROI). The original image 610 of the ROI corresponds to a section of the orbital bone structure with weak signal contrast due to its very thin bony structure. This is evident by the histogram 620 of the original image 610 indicating that the image consists of mostly dark background pixels without a significant amount of bright pixels highlighting the bone structure. Applying the above thresholding process to convert the original image 610 to binary black and white results in image 630. Such thresholding process may yield gaps and holes in the post-processed images. To tackle this issue, a filling process can be performed on the pre-thresholded image 630 to generate the filled image 640 to further smoothen the boundary between the foreground and the background. Next, an active contour algorithm is applied to the filled image 640 to further refine the boundary resulting in the contoured image 650. The boundary in the contoured image 650 can be further smoothed out to create the final image 660.

Figure 7:
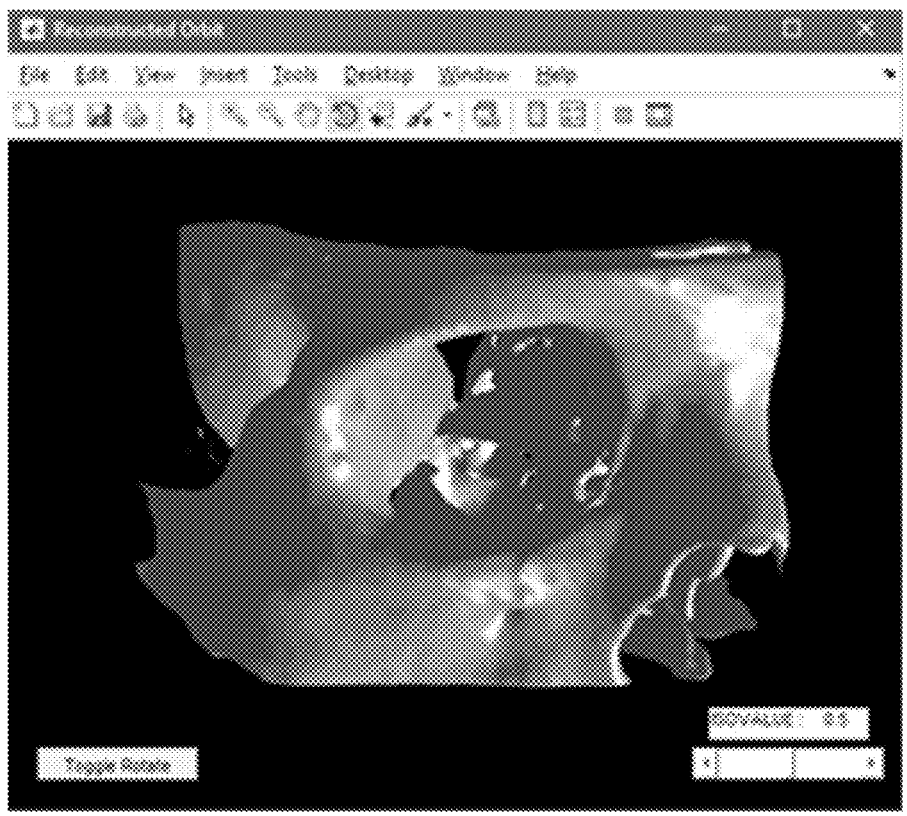
FIG. 7 illustrates an example of a 3D model of an orbital region generated using the marching cubes algorithm.

After the above image processing, the binary segmented 2D images can then be stacked up using the marching cubes algorithm to reconstruct an isosurface. An isosurface is used to represent regions of a particular density in a 3D CT scan, and is used as a visualization tool for 3D imaging. An example of a 3D model of an orbital region generated using the marching cubes algorithm to reconstruct the isosurface is shown in FIG. 7. An additional smoothing process (e.g., Gaussian smoothing) can be performed on the 3D model. Model data for the resulting 3D model of the region of interest for the fractured orbit and the corresponding region for the intact eye orbit can then be mirrored and outputted. The model data represents the preinjured anatomical orbital model of the fractured orbit and can be used to create a pair of negative implant molds and orbital retractor instrument to assist the repair of the fractured orbit. The 3D model data can be outputted to a stereolithography file format (.stl) for 3D printing process.

Figure 8:
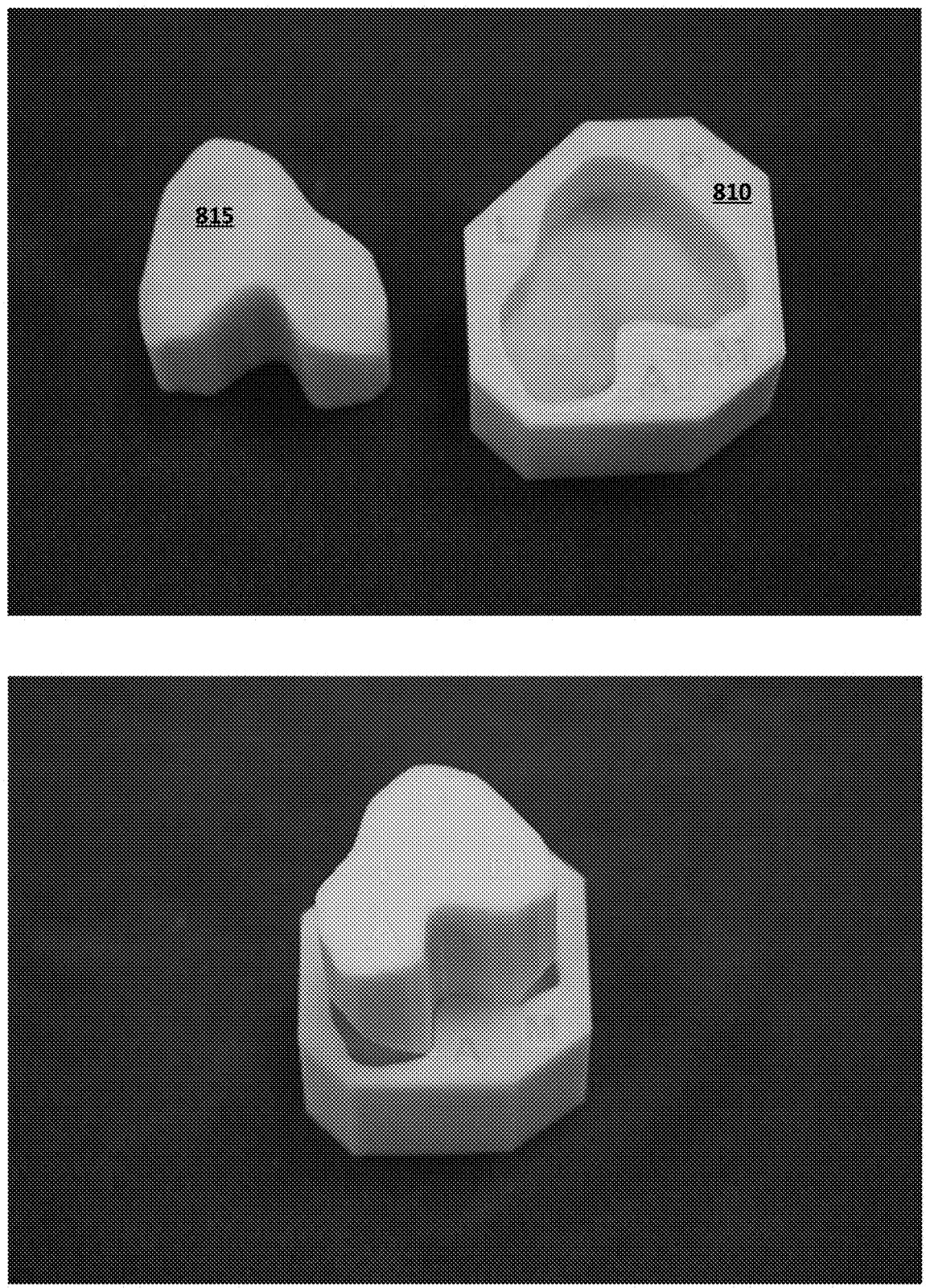
FIG. 8 illustrates examples of 3D printed molds.

FIG. 8 illustrates examples of 3D printed molds. The model data can be used to generate either a negative mold or a positive mold. A patient-specific orbital implant can be formed by pressing any commercially available biocompatible sheet implant against the molds. For example, a patient-specific orbital implant can be formed by placing an implant sheet between mold 810 and 815 and pressing these two molds against each other. The orbital implant can be used to cover the bony defect during operation. The orbital implant can be made from a material having anti-microbial and anti-inflammatory with minimal scar-forming properties.

Figure 10:
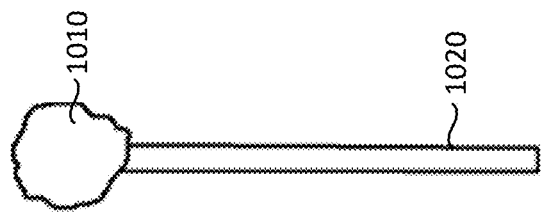
FIG. 10 illustrates a diagram of an orbital retractor.
Figure 9:
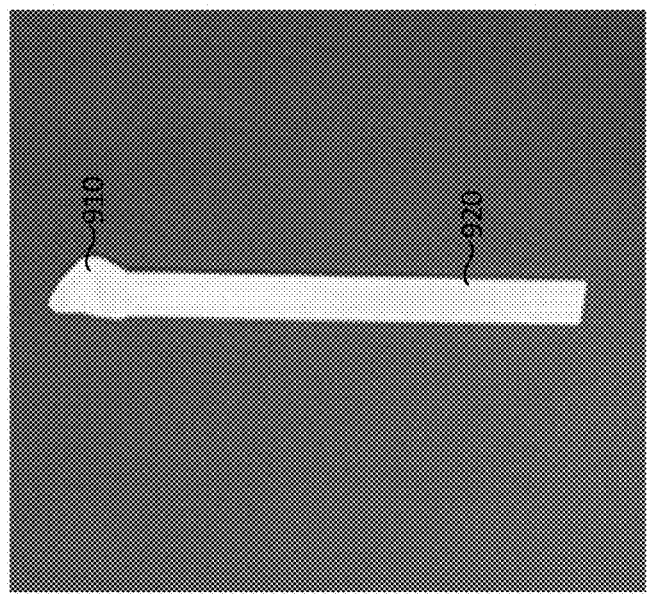
FIG. 9 illustrates an example of an orbital retractor.

The mold produced using the image processing techniques described herein can also be used to fabricate an orbital retractor, which is a tool used for orbital fracture repair operation. FIG. 9 illustrates an example of an eye orbital retractor produced using the image processing techniques described herein, and FIG. 10 illustrates a diagram of an eye orbital retractor. The eye orbital retractor may include a handle (e.g., 920, 1020) and a tip portion (e.g., 910, 1010) connected to the handle. The handle can be held by a surgeon during operation. The handle can be approximately 150 mm long by 0.75 mm thick. The orbital retractor can be used to retract soft tissues of the orbit to improve access to the fracture site. Extreme care should be taken to protect the contents of the eye socket during surgery with minimal risk of trauma. As such, it would be advantageous if the shape of the tip of the eye orbital retractor can conform to the topography of the eye orbit of the patient. Accordingly, the tip of the eye orbital retractor can be formed from the mold generated by the image processing techniques described herein such that the tip of the retractor is tailored for the orbital topography of the patient. In other words, the shape of the tip portion of the patient-specific retractor, which will be inserted into the orbital region of the patient, can be derived from the shape of the mold. By shaping the tip of the retractor according to the orbital structure of the patient, the risk of further damaging the eye orbit region during operation can be reduced.

Figure 11:
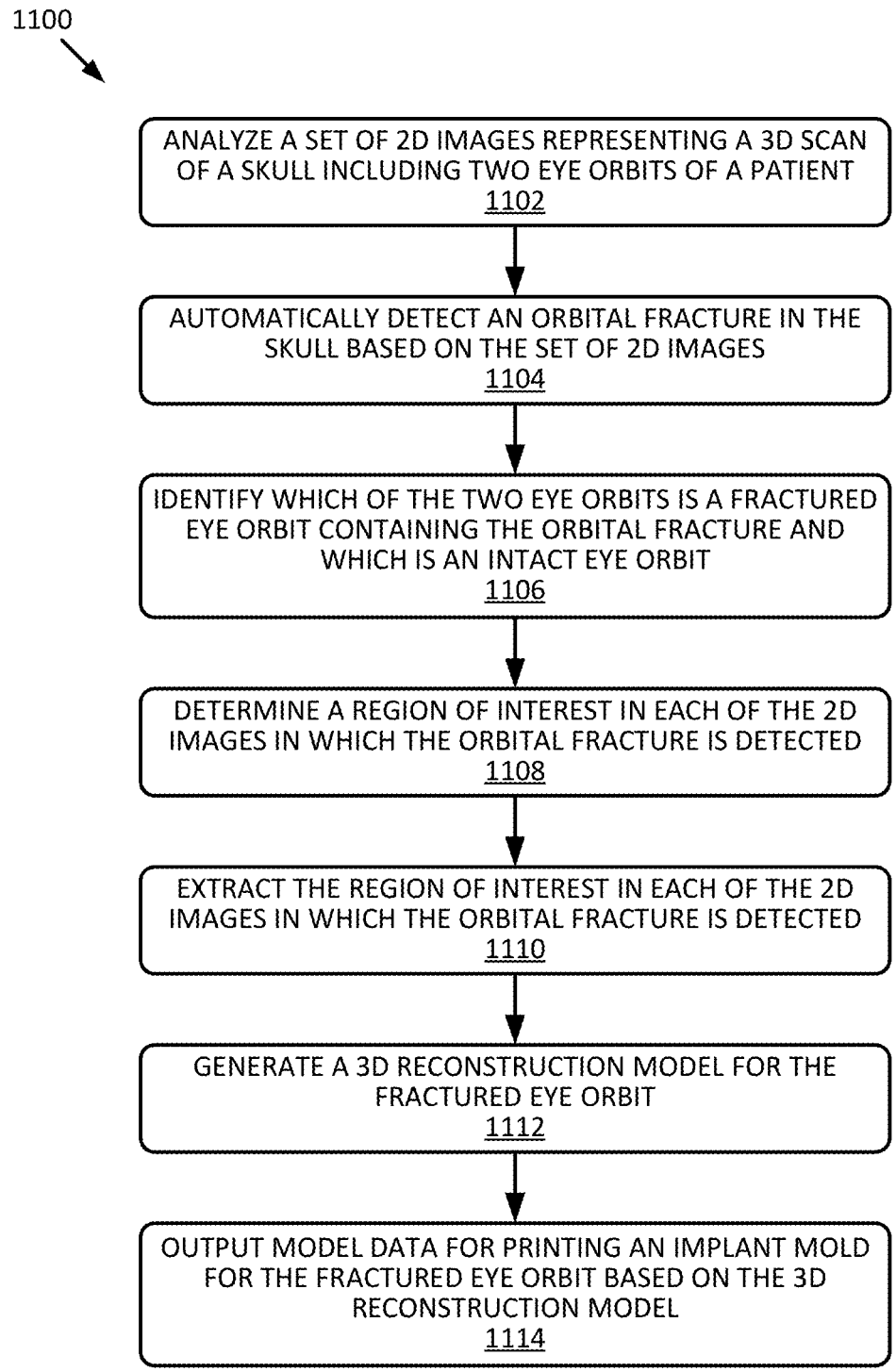
FIG. 11 illustrates a flow diagram of a process for fabricating an orbital implant.

FIG. 11 illustrates a flow diagram of a process 1100 for facilitating fabrication of an orbital implant. Process 1100 can be performed, for example, by an image processing system. Initially, the image processing system can be trained with machine learning to detect orbital fractures in medical images. The training process may use multiple fractured orbital images and multiple intact orbital images, and the system can be trained to detect discontinued orbital bone structure and soft tissue prolapse outside of the orbital region into the surrounding paranasal sinuses as signs of an orbital fracture.

Once the system has been trained to detect orbital fractures, process 1100 may begin by reading a set of medical images from a new patient. The set of medical images may include a set of two-dimensional (2D) images representing a three-dimensional (3D) scan of at least a portion of the skull including two eye orbits of the patient. For example, the medical images can be a computed tomography (CT)

scan of the skull of the patient. The set of 2D images can be presented in sequence on a user interface such as a display, and the system may allow a user to select any of the images for viewing.

At operation 1102, the system analyzes the set of 2D images and may focus on the eye orbit regions of the skull in the images. The analysis may go through each image and identify certain properties or characteristics in each image such as discontinued orbital bone structure, prolapse of orbital tissues, asymmetry between the left and right eye orbit, etc. A classifier derived from the training process can be used to classify these properties or characteristics and determine whether an image contains any orbital bone fracture.

At operation 1104, the system automatically detects the presence of an orbital fracture in the skull of the patient based on the set of 2D images. For example, the system may detect an orbital fracture in one or more of the 2D images. At operation 1106, the system identifies which of the two eye orbits (left or right) is the fractured eye orbit containing the orbital fracture, and which of the two eye orbits (left or right) is the intact eye orbit. The system may tag the images exhibiting the fracture and indicate which eye orbit is the injured eye orbit.

At operation 1108, a region of interest is determined in each of the 2D images in which the orbital fracture is detected. The system may automatically determine the region of interest by creating a boundary around the identified fracture. The boundary can be configured to be in the form of a geometric shape (e.g., circular such as ellipse, circle, etc. or polygon such as triangle, rectangle, etc.), or can take on an irregular shape. The region of interest can be defined by a user. For example, a user may highlight the boundary of the orbital fracture on the image via a user interface to define the region of interest. The region of interest for the fractured eye orbit can then be mirrored to the intact eye orbit to define a corresponding region of interest of the intact eye orbit. The region of interest for the intact eye orbit can be mirrored to recreate the structure needed to fill in or to repair the fractured eye orbit.

At operation 1110, the region of interest is extracted for further processing in each of the 2D images in which the orbital fracture is detected. Extracting the region of interest can reduce the subsequent image processing time by omitting regions that are away from the fracture or images that do not show or exhibit the fracture, and processing only the region of interest within and surrounding the fracture.

At operation 1112, the system may generate a 3D reconstruction model for repairing the fractured eye orbit. In some embodiments, this may include, for each of the two-dimensional images in which the orbital fracture is detected, adaptively enhancing the contrast of the extracted region of interest, converting greyscale color into a binary black and white, segmenting irregular boundaries using an active contour algorithm, and/or applying a marching cubes algorithm to generate an isosurface for the 3D reconstruction model. The 3D reconstruction model can be used to determine the size, shape, and topography of an implant needed to repair the fractured eye orbit such that the fractured eye orbit can resemble as much as possible a mirror image of the intact eye orbit.

At operation 1114, model data based on the 3D reconstruction model, which can be used to generate an implant mold for the fractured eye orbit is outputted. For example, the model data for generating the implant mold can be outputted in a stereolithographical file format, and a .stl file compatible for 3D printing can be generated. The model data (e.g., .stl file) can then be transferred to a 3D printer to print an implant mold. The implant mold can then be used to fabricate a patient-specific orbital bone implant using biocompatible material.

Figure 12:
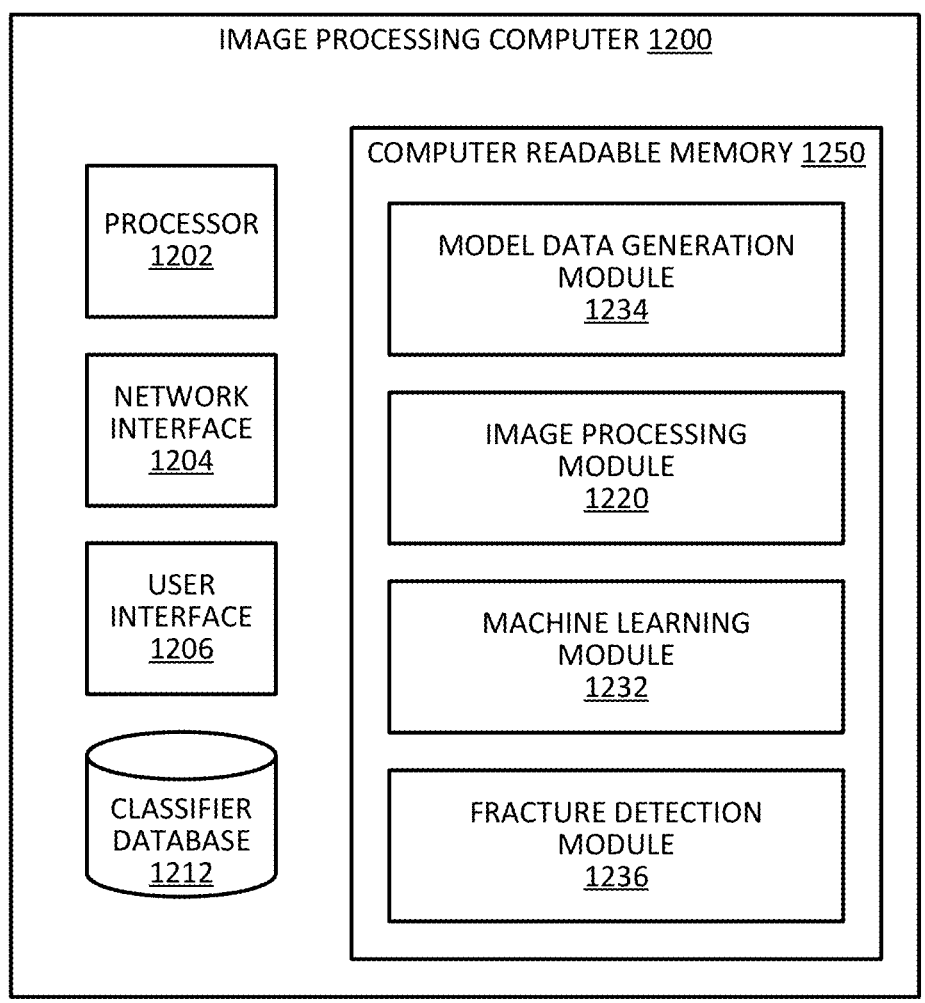
FIG. 12 illustrates an image processing system.

FIG. 12 illustrates an image processing system 1200 that can be used to implement the various image processing techniques described herein, according to some embodiments. Image processing system 1200 may include a processor 1202, a network interface 1204, a user interface 1206, a classifier database 1212, and a computer readable memory 1250 storing code executable by processor 1202. The image processing system 1200 can be a standalone computing device or can be integrated with or communicatively coupled to a CT scanner or other medical imaging machinery. A 3D printer can also be communicatively coupled to image processing system 1200.

Processor 1202 can be implemented as one or more integrated circuits (e.g., one or more single core or multicore microprocessors and/or microcontrollers) and is used to control the operation of image processing system 1200. Processor 1202 can execute a variety of programs in response to program code or computer-readable code stored in memory 1250 and can maintain multiple concurrently executing programs or processes. The processor 1202 may include an arithmetic logic unit (ALU) to perform data manipulation using mathematical operations. The image processing system 1000 may include a dedicated ALU separate from processor 1202.

Network interface 1204 may include one or more transceivers, connectors, or I/O ports that can be used by image processing system 1200 to communicate with other devices, to connect with external networks, and/or to transfer data using electronic or physical medium. User interface 1206 can include any combination of input and output elements (e.g., pointer device, speaker, display, etc.) to allow a user to interact with and invoke the functionalities of image processing system 1200. The user interface 1206 may include an integrated display (e.g., flat panel display, touch screen, etc.) or can be coupled to an external display.

Computer readable memory 1250 can be implemented using any combination of volatile memories (e.g., DRAM, SRAM), non-volatile memories (e.g., flash memory), and/or any other non-transitory storage medium, or a combination thereof media. Memory 1250 may store an operating system and a variety of programs and/or algorithms. For example, memory 1250 may store a machine learning module 1232, a fracture detection module 1236, an image processing module 1220, and a model data generation module 1234. These modules can be integrated in any combination, and/or can be part of one or more software applications.

Machine learning module 1232 may provide functionalities to train image processing system 1200 to detect orbital bone fractures in medical images. For example, machine learning module 1232 may identify characteristics or properties of control or known images exhibiting orbital bone fractures, compare those characteristics or properties with control or known images exhibiting only intact orbital bone structure. These characteristics or properties can be classified and stored in classifier database 1212.

Fracture detection module 1236 may provide functionalities to detect orbital bone fractures in medical images of an actual patient. Fracture detection module 1236 may analyze the medical images of any patient and compare characteristics or properties of the scans with those stored in classifier database 1212 to determine if the patient has an orbital fracture. Fracture detection module 1236 may also extract a region of interest from the images exhibiting the orbital fracture for further image processing.

Image processing module 1220 may provide functionalities to enhance the image quality of the extracted region of interest. For example, image processing module 1020 may enhance the contrast of the extracted images to improve the visual distinction of the orbital bone structure. An adaptive contrast enhancement technique can be used to adjust the pixel intensity based on the intensities of the surrounding pixels. Image processing module 1220 may also convert the extracted images from greyscale into binary black and white using a thresholding process. Image processing module 1220 may further segment and smooth out the boundaries of the orbital bone structure using an active contour technique. The resulting enhanced images can be used to generate a 3D reconstruction model of the orbital bone structure.

Model data generation module 1234 may provide functionalities to build a 3D model of the orbital bone structure from the enhanced 2D images. For example, model data generation module 1234 may apply a marching cubes algorithm to the enhanced 2D images to generate the 3D model. The 3D model data can be converted into stereolithographical data and be outputted as a .stl file. The model data can be provided, for example, to a 3D printer to produce a mold that can be used to fabricate a patient-specific orbital implant.

Accordingly, the techniques described herein can be used to improve pre-operational preparation and shorten the waiting time required before operating on patients suffering from orbital bone fractures. The fabrication of orbital implants and operation tools such as retractors that can conform to the topography of the particular patient's orbital bone structure which can reduce implant fitting time and reduce risk of tissue trauma during operation.

The techniques described herein may involve implementing one or more functions, processes, operations or method steps. The functions, processes, operations or method steps may be implemented as a result of the execution of a set of instructions or software code by a suitably-programmed computing device, microprocessor, data processor, or the like. The set of instructions or software code may be stored in a memory or other form of data storage element which is accessed by the computing device, microprocessor, etc. The set of instructions or software code may be stored on a computer readable medium, such as a random access memory (RAM), a read only memory (ROM), flash memory, a magnetic medium such as a hard-drive or a floppy disk, a steady state drive, or an optical medium such as a CD-ROM. Any such computer readable medium may reside on or within a single computational apparatus and may be present on or within different computational apparatuses within a system or network. The functions, processes, operations or method steps may be implemented by firmware or a dedicated processor, integrated circuit, processing unit (e.g., ALU), etc.

The methods and processes described herein are exemplary in nature, and the methods and processes in accordance with some embodiments may perform one or more of the steps in a different order than those described herein, include one or more additional steps not specially described, omit one or more steps, combine one or more steps into a single step, split up one or more steps into multiple steps, and/or any combination thereof. One or more features from any embodiment may be combined with one or more features of any other embodiment without departing from the scope of the invention.

A recitation of "a," "an," or "the" is intended to mean "one or more" unless specifically indicated to the contrary.

What is claimed is:

1. A method comprising:
    analyzing, by an image processing system, a set of two-dimensional images representing a three-dimensional scan of at least a portion of a skull including two eye orbits of a patient;
    automatically detecting, by the image processing system, an orbital fracture in the skull based on the set of two-dimensional images;
    identifying, by the image processing system, which of the two eye orbits is a fractured eye orbit containing the orbital fracture and which is an intact eye orbit;
    determining, by the image processing system, a region of interest in each of the two-dimensional images in which the orbital fracture is detected;
    extracting, by the image processing system, the region of interest in each of the two-dimensional images in which the orbital fracture is detected;
    generating, by the image processing system, a three-dimensional reconstruction model for the fractured eye orbit; and
    outputting, by the image processing system, model data for generating an implant mold for the fractured eye orbit based on the three-dimensional reconstruction model.

2. The method of claim 1, further comprising:
    training the image processing system to detect the orbital fracture using multiple fractured orbital images and multiple intact orbital images.

3. The method of claim 1, wherein training the image processing system to detect the orbital fracture includes training the image processing system to detect discontinued orbital bone structure and soft tissue prolapse outside of an orbital region into surrounding paranasal sinuses as indications of a presence of orbital fracture.

4. The method of claim 1, wherein generating the three-dimensional reconstruction model includes, for each of the two-dimensional images in which the orbital fracture is detected, adaptively enhancing a contrast of the extracted region of interest.

5. The method of claim 4, wherein generating the three-dimensional reconstruction model further includes, for each of the two-dimensional images in which the orbital fracture is detected, converting greyscale color into a binary black and white.

6. The method of claim 5, wherein generating the three-dimensional reconstruction model further includes, for each of the two-dimensional images in which the orbital fracture is detected, segmenting irregular boundaries using an active contour algorithm.

7. The method of claim 6, wherein generating the three-dimensional reconstruction model includes applying a marching cubes algorithm to generate an isosurface for the three-dimensional reconstruction model.

8. The method of claim 1, wherein the model data for generating the implant mold is in a stereolithographical file format.

9. The method of claim 1, further comprising 3D printing the implant mold using the model data.

10. The method of claim 1, further comprising fabricating an orbital implant using the implant mold.

11. The method of claim 1, further comprising fabricating a tip portion of an eye orbital retractor using the implant mold.

12. The orbital implant produced by the method of claim 10, wherein the orbital implant conforms to a topography of the fractured eye orbit of the patient.

13. An eye orbital retractor comprising:
a handle portion; and
the tip portion produced by the method of claim 11, wherein the tip portion conforms to a topography of an eye orbit of the patient.

14. An image processing system comprising:
a processor; and
a memory coupled to the processor, the memory storing a set of instructions, which when executed by the processor, causes the image processing system to:
analyze a set of two-dimensional images representing a three-dimensional scan of at least a portion of a skull including two eye orbits of a patient;
detect an orbital fracture in the skull based on the set of two-dimensional images;
identify which of the two eye orbits is a fractured eye orbit containing the orbital fracture and which is an intact eye orbit;
determine a region of interest in each of the two-dimensional images in which the orbital fracture is detected;
extract the region of interest in each of the two-dimensional images in which the orbital fracture is detected;
generate a three-dimensional reconstruction model for the fractured eye orbit; and
output model data for generating an implant mold for the fractured eye orbit based on the three-dimensional reconstruction model.

15. A non-transitory computer readable medium storing code, which when executed by a processor, implements operations comprising:
analyzing a set of two-dimensional images representing a three-dimensional scan of at least a portion of a skull including two eye orbits of a patient;
automatically detecting an orbital fracture in the skull based on the set of two-dimensional images;
identifying which of the two eye orbits is a fractured eye orbit containing the orbital fracture and which is an intact eye orbit;
determining a region of interest in each of the two-dimensional images in which the orbital fracture is detected;
extracting the region of interest in each of the two-dimensional images in which the orbital fracture is detected;
generating a three-dimensional reconstruction model for the fractured eye orbit; and
outputting model data for generating an implant mold for the fractured eye orbit based on the three-dimensional reconstruction model.

16. The non-transitory computer readable medium of claim 15, wherein the operations further comprise:
using machine learning for orbital fracture detection training.

17. The non-transitory computer readable medium of claim 15, wherein generating the three-dimensional reconstruction model includes, for each of the two-dimensional images in which the orbital fracture is detected, adaptively enhancing a contrast of the extracted region of interest.

18. The non-transitory computer readable medium of claim 17, wherein generating the three-dimensional reconstruction model further includes, for each of the two-dimensional images in which the orbital fracture is detected, converting greyscale color into a binary black and white.

19. The non-transitory computer readable medium of claim 18, wherein generating the three-dimensional reconstruction model further includes, for each of the two-dimensional images in which the orbital fracture is detected, segmenting irregular boundaries using an active contour algorithm.

20. The non-transitory computer readable medium of claim 19, wherein generating the three-dimensional reconstruction model includes applying a marching cubes algorithm to generate an isosurface for the three-dimensional reconstruction model.

* * * * *